(12) United States Patent
Potts

(10) Patent No.: US 7,591,167 B2
(45) Date of Patent: Sep. 22, 2009

(54) METHODS AND SYSTEMS FOR MEASUREMENT OF TIRE ROLLING RESISTANCE

(76) Inventor: Gerald R. Potts, 3422 Bancroft Rd., Akron, OH (US) 44333

(*) Notice: Subject to any disclaimer, the term of this patent is extended or adjusted under 35 U.S.C. 154(b) by 0 days.

(21) Appl. No.: 11/943,582

(22) Filed: Nov. 20, 2007

(65) Prior Publication Data

US 2008/0115563 A1    May 22, 2008

Related U.S. Application Data

(60) Provisional application No. 60/866,446, filed on Nov. 20, 2006.

(51) Int. Cl.
*G01N 19/02* (2006.01)
(52) U.S. Cl. .......................................................... 73/9
(58) Field of Classification Search .................. 73/8, 73/9, 146
See application file for complete search history.

(56) References Cited

U.S. PATENT DOCUMENTS

| | | | | |
|---|---|---|---|---|
| 3,862,570 A | * | 1/1975 | Ongaro | 73/146 |
| 4,197,736 A | * | 4/1980 | Barrett | 73/862 |
| 4,238,954 A | * | 12/1980 | Langer | 73/146 |
| 4,344,324 A | * | 8/1982 | Langer | 73/146 |
| 4,458,527 A | * | 7/1984 | McFarland et al. | 73/146 |
| 4,584,873 A | * | 4/1986 | Ongaro | 73/146 |
| 4,691,564 A | * | 9/1987 | Potts et al. | 73/146 |
| 4,856,324 A | * | 8/1989 | Potts | 73/146 |
| 4,949,574 A | * | 8/1990 | Linden et al. | 73/146 |
| 5,317,912 A | * | 6/1994 | Mallison | 73/146 |
| 5,323,646 A | * | 6/1994 | Poling, Sr. | 73/146 |
| 5,448,910 A | * | 9/1995 | Yurjevich et al. | 73/146 |
| 5,542,618 A | * | 8/1996 | Andersen | 241/227 |
| 6,655,202 B2 | * | 12/2003 | Potts et al. | 73/146 |
| 6,799,470 B2 | * | 10/2004 | Harada | 73/774 |

* cited by examiner

*Primary Examiner*—Lisa M Caputo
*Assistant Examiner*—Freddie Kirkland, III
(74) *Attorney, Agent, or Firm*—Dwight A. Stauffer, Patent Agent

(57) ABSTRACT

Method and apparatus for testing tires to measure the rolling resistance generated while a tire rolls under a radial load, the method including the steps of mounting two tires on spindles having substantially parallel axes; wherein the two tires are substantially equivalent and have substantially equal inflation pressures; loading a first one of the tires against a second one of the tires, tread-to-tread, at a predetermined tire-to-tire test load, then measuring a distance between axes of the two tire spindles; rotating one of the tires such that it rotates the other tire; measuring the total torque required to rotate the two tires at a predetermined rotation rate; and calculating the average rolling resistance of the two tires by dividing the value of total torque by the distance between the axes of the two tire spindles. Alternatively measure force at each spindle, equating each force to that tire's rolling resistance.

2 Claims, 4 Drawing Sheets

METHODS AND SYSTEMS FOR MEASUREMENT OF TIRE ROLLING RESISTANCE

CROSS-REFERENCE TO RELATED APPLICATIONS

This application claims the benefit of U.S. Provisional Patent Application No. 60/866,446, filed Nov. 20, 2006 by Gerald R. Potts.

TECHNICAL FIELD OF THE INVENTION

The present invention pertains generally to the measurement of rolling resistance of loaded rolling vehicle tires.

BACKGROUND OF THE INVENTION

Tire Rolling Resistance ("RR") tests have been performed for many years, but especially since the energy crisis of 1973. Referring to the prior art drawing of FIG. 1, such tests are commonly performed on a roadwheel tester 15 by loading a tire 110 against the cylindrical surface of a roadwheel 30 that has a diameter greater than 48 inches, usually of 67.23 inches diameter. RR tests on a round roadwheel have been found to correlate well with vehicle coastdown tests as long as the roadwheel diameter exceeds 48 inches. Roadwheel tests became the norm for measuring tire RR in the 1980's with the Society of Automotive Engineers publication of its Recommended Practice J1269 and later J2452. While road wheel tests give results that correlate with flat footprint tests, the result is a higher measured RR than a flat footprint would generate due to the round (cylindrical) roadwheel surface which causes a reverse curvature of the tire 110 in the area of its footprint 33, which is not representative of actual tire service.

Therefore tire and vehicle engineers have always been interested in performing RR testing by loading a test tire 110 against a flat surface test machine 35, for example the Flat-Trac® tire test machine illustrated in FIG. 2A, which is sold by MTS Systems Corporation of Eden Prairie, Minn., USA. Referring to the FIG. 2B schematic view of a prior art flat surface test machine 35, a test tire 110 is loaded against a flat section of a running belt 37 with a loading force of, for example, 1,000 pounds. A flat support surface 39 under the belt 37 counters the tire loading force to keep the belt flat. To control frictional drag, water 41 is forced between the belt 37 and the support surface 39 to provide a hydrodynamic bearing.

There are several problems inherent in rolling resistance tests performed on existing flat surface test machines 35. A major problem is due to an unknown road surface inclination angle that is created by a water wedge of the hydrodynamic bearing supporting the flat track against which the tire is loaded. In effect the hydrodynamic bearing presents the road surface to the tire at a small, but unknown, inclination angle that causes uncertainty in the RR test results. A paper presented by Lloyd of the General Motors Proving Ground (Stephen E. Lloyd; "Development of a Flat Surface Rolling Resistance Test Facility"; SAE Paper 780636; Jun. 5, 1978) described a flat surface test machine especially constructed for rolling resistance tests, but which was later dismantled due to the unknown footprint inclination angle that influenced the measurements by an unknown amount.

Another problem is that the prior art flat surface testers 35 are not only expensive to purchase, but the cost of running RR tests on them is generally too high for the test volume required. Therefore the MTS Systems Corporation is offering a variant flat surface tire tester 45 as shown schematically in FIG. 3. Such a test machine 45 could be made for less cost than the full force and moment flat surface tire tester 35. Furthermore, the variant tester 45 economizes by testing two tires 110a, 110b (collectively referred to as tires 110) simultaneously. However, the measurement errors caused by the water wedge 41 still need to be addressed.

BRIEF SUMMARY OF THE INVENTION

According to the invention, a method is disclosed for testing tires to measure the rolling resistance generated while a tire rolls under a radial load, the method comprising the steps of: mounting two tires on spindles having substantially parallel axes; wherein the two tires are substantially equivalent and have substantially equal inflation pressures; loading a first one of the tires against a second one of the tires, tread-to-tread, at a predetermined tire-to-tire test load, then measuring a distance between axes of the two tire spindles; rotating one of the tires such that it rotates the other tire; measuring the total torque required to rotate the two tires at a predetermined rotation rate; and calculating the average rolling resistance of the two tires by dividing the value of total torque by the distance between the axes of the two tire spindles, as measured while the tires are rotating at a predetermined rate under a predetermined test load.

According to the invention, the method further comprises the steps of: selecting a third tire that is substantially equivalent to the first and second tires, including substantially equal inflation pressures; repeating the steps of claim 1 with the first tire and the third tire, thereby determining the average rolling resistance of the first tire and the third tire; again repeating the steps of claim 1 with the second tire and the third tire, thereby determining the average rolling resistance of the second tire and the third tire; and using the data for the three tests with the first, second, and third tires in an algebraic solution for the individual rolling resistance values of the first, second, and third tires.

According to the invention, the method further comprises the steps of: selecting a third tire and a fourth tire, both of which are substantially equivalent to the first and second tires, including substantially equal inflation pressures; repeating the steps of claim 1 with the third tire and the fourth tire, thereby determining the average rolling resistance of the third tire and the fourth tire; and averaging the results of the two two-tire tests to determine the average rolling resistance of the first, second, third and fourth tires combined.

According to the invention, a method is disclosed for testing tires to measure the rolling resistance generated while a tire rolls under a radial load, the method comprising the steps of: mounting two tires on spindles having substantially parallel axes; wherein the two tires are substantially equivalent and have substantially equal inflation pressures; loading a first one of the tires against a second one of the tires, tread-to-tread, at a predetermined tire-to-tire test load; rotating one of the tires such that it rotates the other tire; measuring force at the spindle of each of the two tires, wherein each spindle force is measured in a direction that is substantially parallel to a footprint interface plane formed by the two tires loaded one against the other; and equating the force measured at the spindle of the first tire to the rolling resistance value for the first tire, and equating the force measured at the spindle of the second tire to the rolling resistance value for the second tire.

According to the invention, a tester for testing tires to measure the rolling resistance generated while a tire rolls under a radial load, comprises: two parallel tire mounting spindles, one of which is connected to a rotational driver such that the driver rotates the one spindle; hubs for securing a tire on each spindle; and a framework that positions tires on the spindles such that they are loaded against each other tread-to-tread at a predetermined loading force.

According to the invention, the framework further comprises placement of the spindles in the same horizontal plane.

According to the invention, the tester further comprises: a torque sensor on the driven spindle.

According to the invention, the tester further comprises: two force sensors, one at each spindle, each being positioned for measuring spindle-to-framework force in a direction that is substantially parallel to a footprint interface plane formed by the two tires loaded one against the other.

Other objects, features and advantages of the invention will become apparent in light of the following description thereof.

BRIEF DESCRIPTION OF THE DRAWINGS

Reference will be made in detail to preferred embodiments of the invention, examples of which are illustrated in the accompanying drawing figures. The figures are intended to be illustrative, not limiting. Although the invention is generally described in the context of these preferred embodiments, it should be understood that it is not intended to limit the spirit and scope of the invention to these particular embodiments.

Certain elements in selected ones of the drawings may be illustrated not-to-scale, for illustrative clarity. The cross-sectional views, if any, presented herein may be in the form of "slices", or "near-sighted" cross-sectional views, omitting certain background lines which would otherwise be visible in a true cross-sectional view, for illustrative clarity.

Elements of the figures can be numbered such that similar (including identical) elements may be referred to with similar numbers in a single drawing. For example, each of a plurality of elements collectively referred to as 199 may be referred to individually as 199a, 199b, 199c, etc. Or, related but modified elements may have the same number but are distinguished by primes. For example, 109, 109', and 109" are three different elements which are similar or related in some way, but have significant modifications. Such relationships, if any, between similar elements in the same or different figures will become apparent throughout the specification, including, if applicable, in the claims and abstract.

Figure 1:
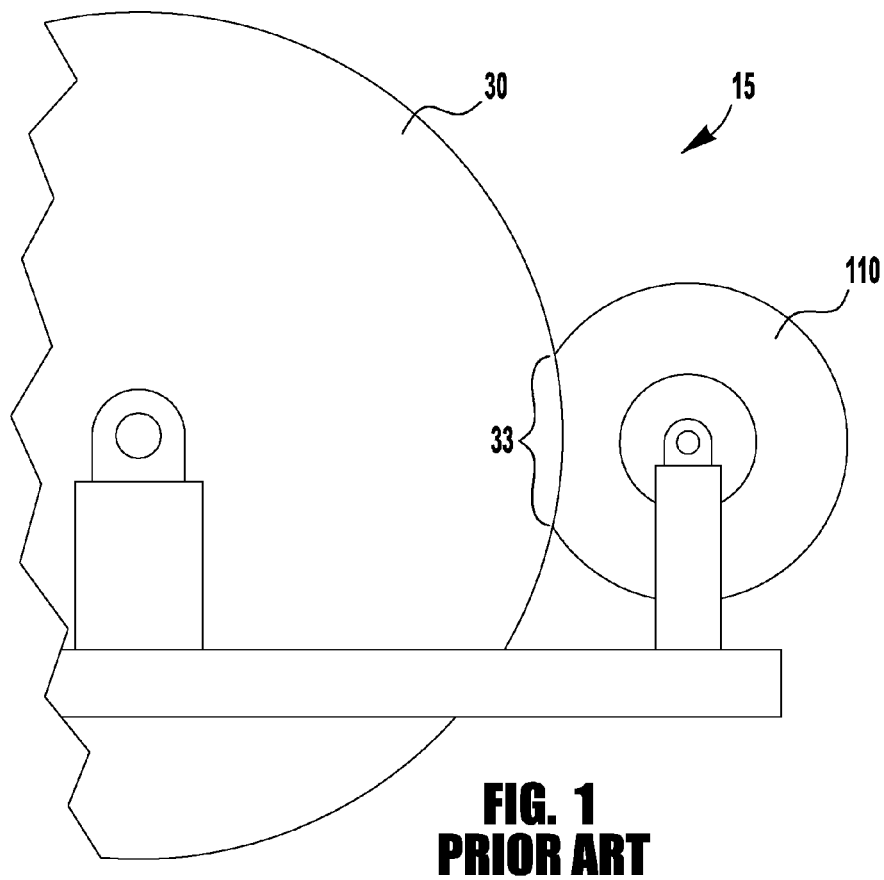

The structure, operation, and advantages of the present preferred embodiment of the invention will become further apparent upon consideration of the following description taken in conjunction with the accompanying drawings, wherein:

FIG. 1 is a schematic view of the most common form of prior art rolling resistance test machine wherein a test tire is loaded against a cylindrical metal roadwheel.

Figure 2B:
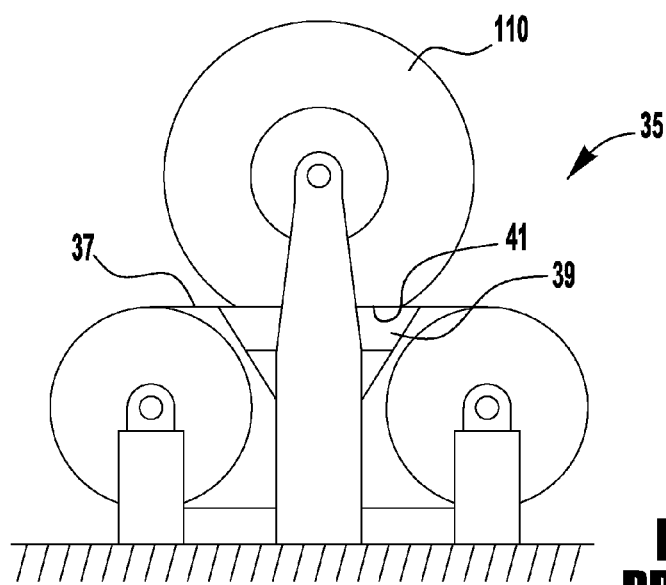
Figure 2A:
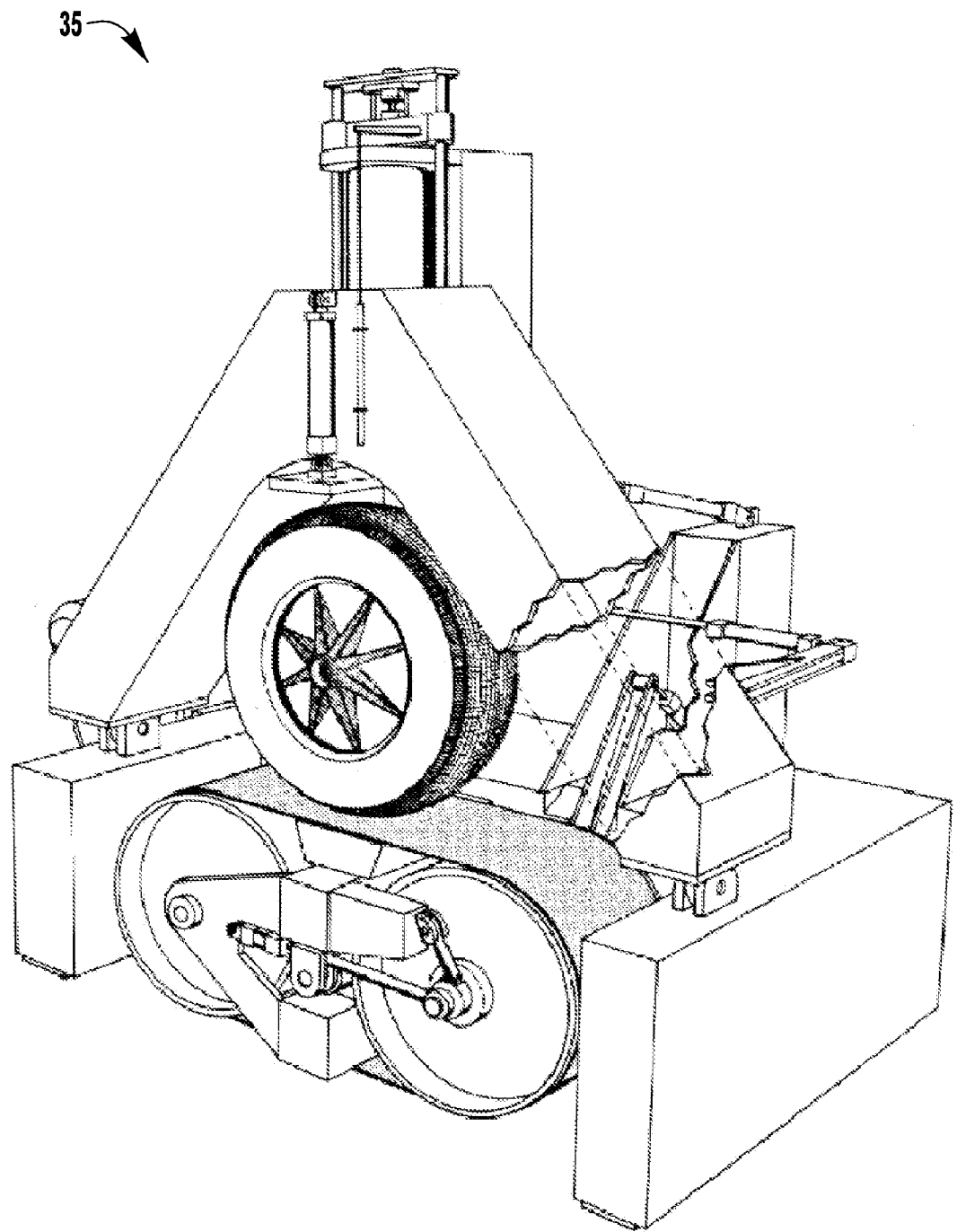

FIG. 2A is a perspective illustration of a complete, prior art, flat surface test machine that loads the test tire against a flat moving beltway.

FIG. 2B is a schematic view of the test concept and major parts of the prior art machine of FIG. 2A.

Figure 3:
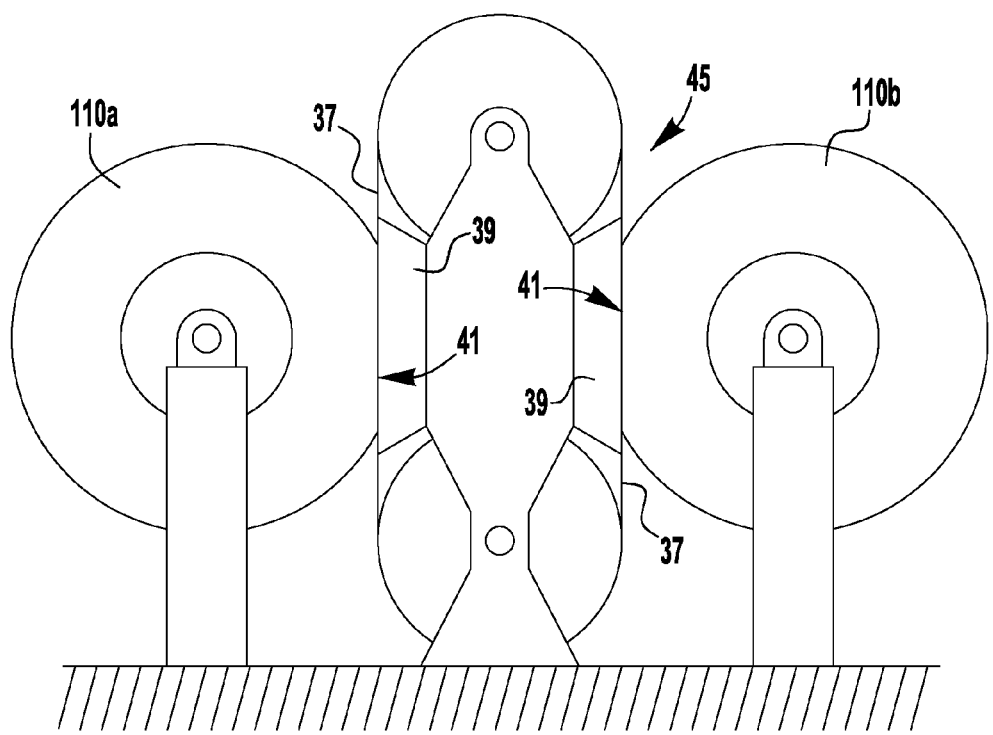

FIG. 3 is a schematic view of a variant, improved version of the prior art flat surface test machine wherein a double-sided flat track enables testing of two tires simultaneously.

Figure 4:
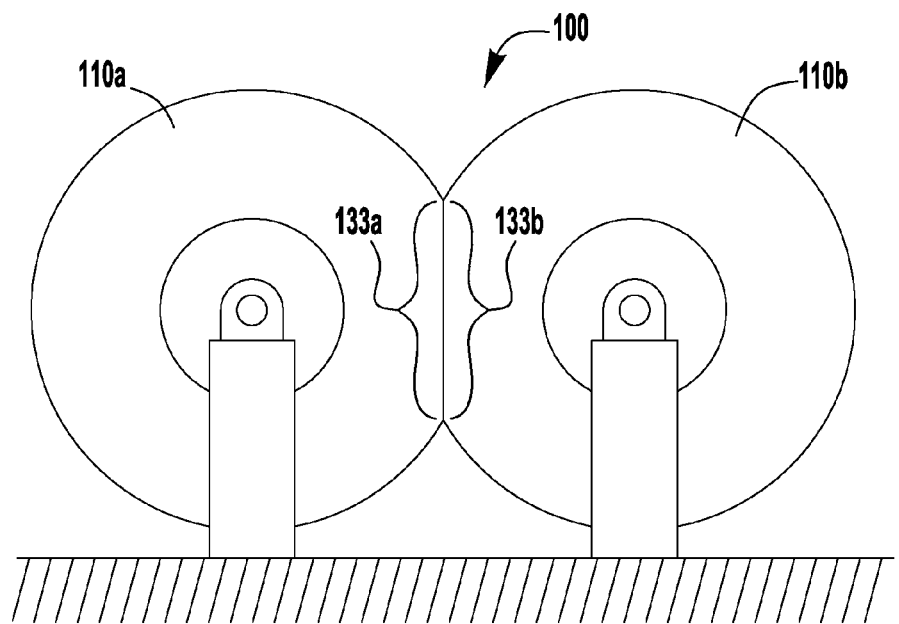

FIG. 4 is a schematic view of the test concept for a two-tire rolling resistance test machine, according to the present invention.

Figure 5:
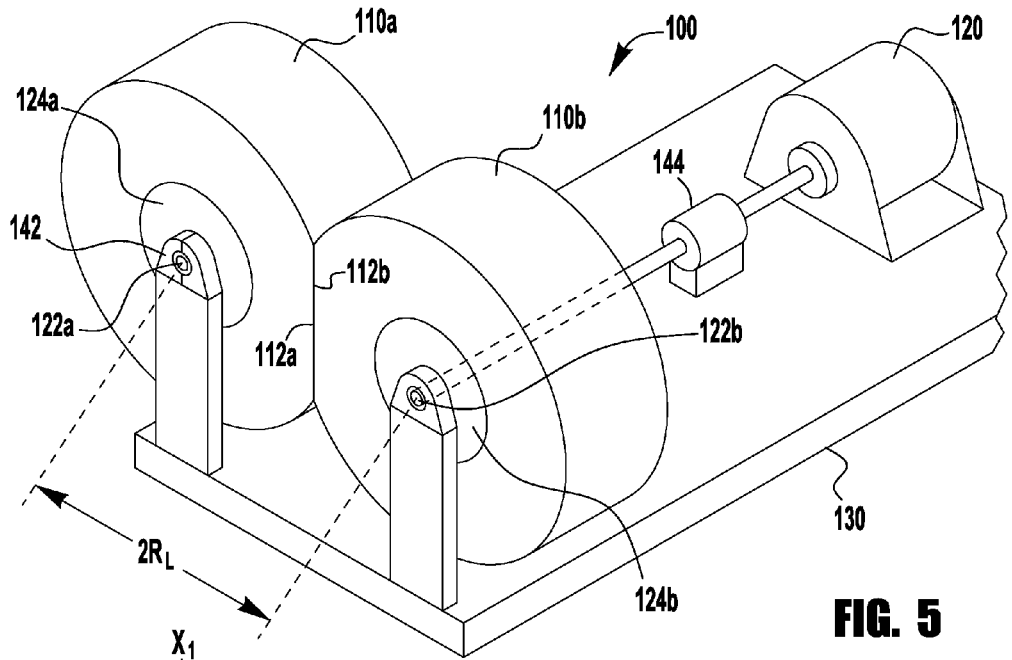

FIG. 5 is a schematic view of the test concept and major parts of a first embodiment of the two-tire tester, according to the present invention.

Figure 6:
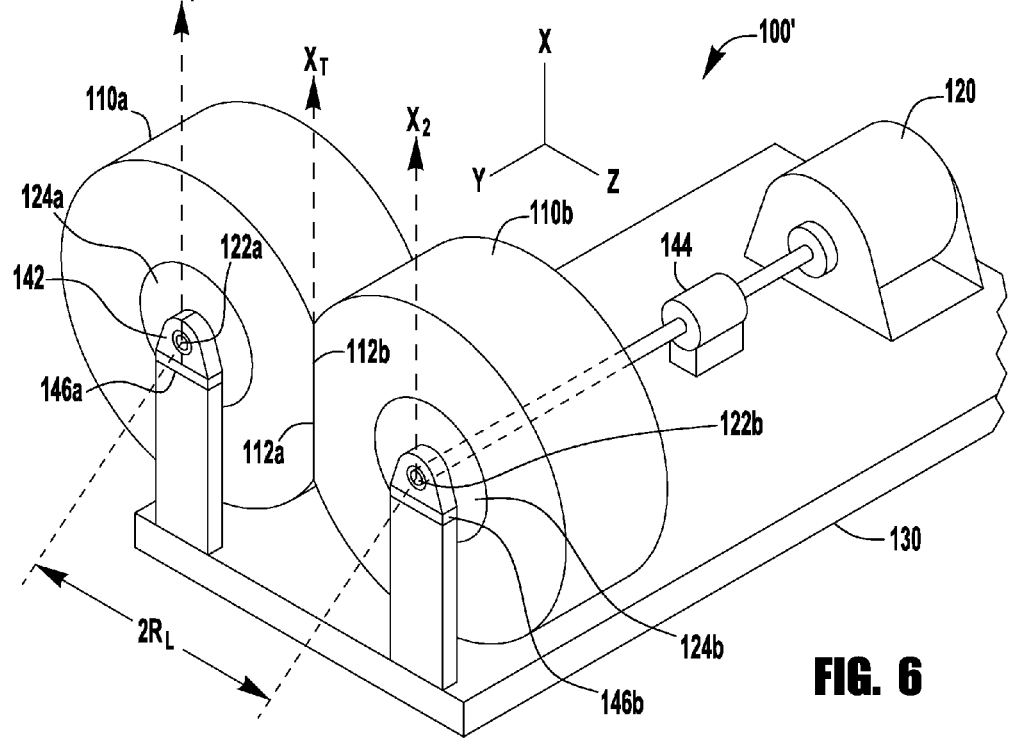

FIG. 6 is a schematic view of the test concept and major parts of a second embodiment of the two-tire tester, having additional measurement capability, according to the present invention.

DETAILED DESCRIPTION OF THE INVENTION

The present invention (a novel testing method and a novel apparatus that implements the novel method) provides a more accurate and simpler, therefore less expensive, flat footprint rolling resistance (RR) test. Not only is the inventive tester (e.g., 100, 100' in FIGS. 5-6) less expensive to build, plus faster and less expensive to operate, but it also solves the measurement accuracy problems inherent in prior art test machines such as the testers 15, 35, 45 that have been described in the background section hereinabove.

Although major components of the test equipment are illustrated and described, it should be understood that the present disclosure focuses on those apparatus elements that are changed from the prior art to create the invention. Other elements that are obviously necessary to carry out the rolling resistance tests are not described because they are substantially already known in the prior art. For example, measurement sensors described herein are assumed to be connected to power supplies, displays, and/or a computer (all not shown) in order to operate the sensors and to carry out calculations of desired values using data measurement signals output by the sensors.

As shown schematically in FIG. 4, the inventive two-tire rolling resistance test machine (e.g., tester 100) loads a first tire 110a against a nominally identical (substantially equivalent) second tire 110b that has a substantially equal inflation pressure so that the tire footprints 133a, 133b form substantially flat mirror images of each other, thus eliminating the prior art unknown footprint inclination angle problem. Furthermore, even if the two tire deflections are not quite equal (due to, for example, slightly different tread stiffness and/or fill pressure), then the higher rolling resistance of one tire's concave footprint (e.g., 133a) will be averaged out by the lower rolling resistance of the opposing tire's convex footprint (e.g., 133b).

FIG. 5 schematically shows a first embodiment of the inventive two-tire tester 100 that loads a first tire 110a against a second tire 110b, tread-to-tread 112, at a predetermined test load "LOAD", with the first and second tires being substantially equivalent including substantially equal inflation pressures P. A rotational driver 120 rotates one of the tires (e.g., 110b) thereby making it a "driving tire" which then rotates the other tire (e.g., 110a), a "driven tire", so that both tires 110 are rotated at a predetermined rotational rate "RATE". A load cell sensor 142 on one tire spindle 122a measures tire loading force Fz (one tire's Fz being equal and opposite to the other tire's Fz), and a torque sensor 144 on the spindle 122b turned by the driver 120 measures the total torque T needed to rotate the two tires 110 together at the predetermined rotation rate against their combined rolling resistances FR1 and FR2. The use of a torque sensor 144 on the driven spindle 122b reduces test time by only requiring testing in one direction of rotation, as opposed to the bi-directional test that is normally run on test machines that directly measure the RR force using a load cell at the single tire's spindle. (The clockwise force and the counterclockwise force must be averaged to get a true reading of force in the x direction, parallel to the flat footprint, by canceling out any z component of force that may be caused by positioning error.)

The rolling resistance force for the two tires combined is:

$$FR1 + FR2 = \frac{T}{R_L}$$

where FR1 and FR2 are the (not-measured) rolling resistances of the first tire 110a and the second tire 110b, respectively; where $R_L$ is the radius of a loaded tire 110 at the middle of its footprint 112 (i.e., the minimum tire radius); and where T is the total torque measured at the driven spindle 122b by the torque cell 144.

The average rolling resistance FR for the two tires 110a, 110b under test is:

$$FR = \frac{FR1 + FR2}{2} = \frac{T}{2R_L}$$

Of course two times the loaded radius $R_L$ is the distance between axes of the two tire spindles 122 while the tires are rotating at the predetermined rate under the predetermined load, as shown in FIG. 5.

If the individual RR values FR1 and FR2 are desired, then a third tire 110 (nominally identical to the first two tires 110, i.e., substantially equivalent including substantially equal inflation pressures P) may be introduced and the test repeated two more times so that the test tire combinations are:

Test A) tire1 and tire2
Test B) tire1 and tire3
Test C) tire2 and tire3 resulting in three two-tire average RR values:

$$FRA = \frac{FR1 + FR2}{2} \quad (\text{test } A)$$

$$FRB = \frac{FR1 + FR3}{2} \quad (\text{test } B)$$

$$FRC = \frac{FR2 + FR3}{2} \quad (\text{test } C)$$

These three equations can then be algebraically solved for the three unknown values FR1, FR2, and FR3 to get individual rolling resistance values for all three tested tires 110.

Sometimes an average RR value is desired for a four tire set. This can be accomplished by running two, two-tire tests, then averaging the results.

$$FRA = \frac{FR1 + FR2}{2} \quad (\text{test } A)$$

$$FRB = \frac{FR3 + FR4}{2} \quad (\text{test } B)$$

$$FR_{avg} = \frac{FR1 + FR2 + FR3 + FR4}{4} = \frac{FRA + FRB}{2}$$

where FRA is the average RR of the first two tires tested; FRB is the average RR for the other two tires tested; and $FR_{avg}$ is the overall average rolling resistance for the four tire set.

Additional measurements using the inventive two-tire tester 100 are possible. For example, there is a possibility of determining a "driven tire RR" on the free rolling tire position (e.g., first tire 110a), and a "driving tire RR" on the torque sensor 144 tire position (e.g., second tire 110b). To do this, the three-tire test would have to be further scrambled in order to test all three tires in both tire positions. Then the measurement results can be plugged into 6 equations and algebraically solved for 6 unknowns: Driving Tire RR for each of the three tires, and Driven Tire RR for each of the three tires.

Another method of RR measurement using the inventive two-tire tester involves modifying it to a second embodiment two-tire tester 100' that is schematically shown in FIG. 6. A force sensor (load cell) 146 is mounted at each of the two spindles 122 and is arranged to directly measure Fx forces, i.e., rolling resistance forces being measured substantially parallel (e.g., in the x direction) to a footprint 112a-112b interface plane (indicated by line $X_T$) that is formed by the two tires 110 loaded one against the other. This arrangement directly yields individual rolling resistance forces FR1, FR2 for each of the tires 110a, 110b in a single two-tire test. In this test, the torque sensor 144 is not needed to calculate the RR values.

For example, in the preferred arrangement shown, the two tires 110 are horizontally beside each other (in the z direction) and thus create a vertical (x direction) footprint pair 112a, 112b, which will have vertical rolling resistance force vectors. Thus a load cell 146 mounted vertically between a spindle 122 and the machine structure 130 that supports the spindle 122 (e.g., mounted under the spindle 122) will measure vertical forces $Fx_1$ in the $X_1$ direction at the first spindle 122a of the first tire 110a and $Fx_2$ in the $X_2$ direction at the second spindle 122b of the second tire 110b. Since they are parallel to the footprint interface plane $X_T$, the force $Fx_1$ will equal the RR force FR1 of the first tire 110a, and the force $Fx_2$ will equal the RR force FR2 of the second tire 110b. Similarly, the load force sensor 142 is attached to the structure 130 and is horizontally beside one of the spindles 122 (e.g., first spindle 122a) in order to measure the load Fz on the tires 110, i.e., the magnitude of force that presses them against each other in the horizontal (z) direction.

In conclusion, an improved tire rolling resistance measurement test apparatus and method have been described, wherein the inventive apparatus implementing the inventive method loads a first tire against a second tire, tread-to-tread, at a predetermined test load, with the first and second tires being substantially equivalent including substantially equal inflation pressures. A rotational driver rotates one of the tires—a driving tire—which then rotates the other, driven, tire so that both tires are rotated at a predetermined rotational rate. A first embodiment of the apparatus has sufficient elements to calculate rolling resistance forces from a torque sensor measurement of the rotational force needed to drive the tires at the predetermined rotational rate under the predetermined load. A second embodiment of the apparatus has two load cells arranged at the two tire spindles for directly measuring per-tire rolling resistance force in a direction that is substantially parallel (x direction) to a footprint interface plane formed by the two tires being tested. As in the first embodiment, another load cell is positioned for measuring tire-to-tire loading force, and the measurements are taken while the tires are driven at a predetermined rotational rate under a predetermined load.

Although the invention has been illustrated and described in detail in the drawings and foregoing description, the same is to be considered as illustrative and not restrictive in character—it being understood that only preferred embodiments have been shown and described, and that all changes and modifications that come within the spirit of the invention are desired to be protected. Undoubtedly, many other "variations" on the "themes" set forth hereinabove will occur to one having ordinary skill in the art to which the present invention most nearly pertains, and such variations are intended to be within the scope of the invention, as disclosed herein.

What is claimed is:

1. A method of testing tires to measure the rolling resistance generated while a tire rolls under a radial load, the method comprising the steps of:
   (a) mounting two tires on spindles having substantially parallel axes; wherein the two tires are substantially equivalent and have substantially equal inflation pressures;
   (b) loading a first one of the tires against a second one of the tires, tread-to-tread, at a predetermined tire-to-tire test load;
   (c) rotating one of the tires such that it rotates the other tire;
   (d) measuring the total torque required to rotate the two tires at a predetermined rotation rate;
   (e) calculating the average rolling resistance of the two tires by dividing the value of the total torque by a distance between the axes of the two tire spindles, as measured while the tires are rotating at the predetermined rotation rate under the predetermined tire-to-tire test load;
   (f) selecting a third tire that is substantially equivalent to the first and second tires, including substantially equal inflation pressures;
   (g) repeating the steps (a) through (e) with the first tire and the third tire, thereby determining the average rolling resistance of the first tire and the third tire;
   (h) again repeating the steps (a) through (e) with the second tire and the third tire, thereby determining the average rolling resistance of the second tire and the third tire; and
   (i) using the data for the three tests with the first, second, and third tires in an algebraic solution for the individual rolling resistance values of the first, second, and third tires.

2. A method of testing tires to measure the rolling resistance generated while a tire rolls under a radial load, the method comprising the steps of:

mounting two tires on spindles having substantially parallel axes; wherein the two tires are substantially equivalent and have substantially equal inflation pressures;

loading a first one of the tires against a second one of the tires, tread-to-tread, at a predetermined tire-to-tire test load;

rotating one of the tires such that it rotates the other tire;

measuring force at the spindle of each of the two tires, wherein each spindle force is measured in a direction that is substantially parallel to a footprint interface plane formed by the two tires loaded one against the other; and equating the force measured at the spindle of the first tire to the rolling resistance value for the first tire, and equating the force measured at the spindle of the second tire to the rolling resistance value for the second tire.

* * * * *